(12) United States Patent
Krieg et al.

(10) Patent No.: US 6,848,313 B2
(45) Date of Patent: Feb. 1, 2005

(54) METHOD AND DEVICE FOR INSPECTING PIPELINES

(75) Inventors: Wolfgang Krieg, Karlsruhe (DE); Achim Hugger, Karlsruhe (DE)

(73) Assignee: PII Pipetronix GmbH, Stutensee (DE)

( * ) Notice: Subject to any disclaimer, the term of this patent is extended or adjusted under 35 U.S.C. 154(b) by 0 days.

(21) Appl. No.: 10/097,264

(22) Filed: Mar. 15, 2002

(65) Prior Publication Data

US 2003/0136195 A1 Jul. 24, 2003

(30) Foreign Application Priority Data

Jan. 22, 2002 (DE) .......................................... 102 02 432

(51) Int. Cl.$^7$ .............................................. G01N 29/00
(52) U.S. Cl. ............................ 73/628; 73/622; 73/623; 73/602; 73/624; 73/625; 73/626; 73/640; 73/641; 73/627
(58) Field of Search ......................... 73/623, 622, 628, 73/602, 624, 625, 626, 627, 640, 641

(56) References Cited

U.S. PATENT DOCUMENTS

| | | | | |
|---|---|---|---|---|
| 4,022,055 A | * | 5/1977 | Flournoy et al. .............. 73/627 |
| 4,055,990 A | * | 11/1977 | Topping ....................... 73/623 |
| 4,718,277 A | * | 1/1988 | Glascock ..................... 73/622 |
| 4,807,484 A | * | 2/1989 | Goedecke .................. 73/865.8 |
| 4,843,896 A | * | 7/1989 | Napeloni et al. ........... 73/866.5 |
| 4,909,091 A | * | 3/1990 | Ellmann et al. ............... 73/623 |
| 5,007,291 A | * | 4/1991 | Walters et al. ................ 73/640 |
| 5,398,560 A | * | 3/1995 | Zollingger et al. ............ 73/623 |
| 5,460,046 A | * | 10/1995 | Maltby et al. ................ 73/623 |
| 5,574,223 A | * | 11/1996 | Kiefer ......................... 73/623 |
| 5,590,659 A | * | 1/1997 | Hamilton et al. ........... 600/447 |
| 5,641,909 A | * | 6/1997 | Kiefer et al. ................. 73/623 |
| 5,648,613 A | * | 7/1997 | Kiefer ......................... 73/611 |
| 5,770,800 A | * | 6/1998 | Jenkins et al. ............... 73/623 |
| 5,907,100 A | * | 5/1999 | Cook .......................... 73/602 |

* cited by examiner

Primary Examiner—Hezron Williams
Assistant Examiner—André K. Jackson
(74) Attorney, Agent, or Firm—Paul Vincent

(57) ABSTRACT

The invention concerns a method and a device for inspecting pipelines, in particular for detecting defects in pipelines by means of ultrasound. Towards this end, measuring sensors transmit ultrasound signals during passage through a pipeline. The signals reflected on boundary regions of a pipeline wall, e.g. surfaces or defects, are then measured and evaluated. The invention is characterized in that partial regions of the measuring sensors (virtual sensors) formed of a plurality of neighboring sensor elements irradiate ultrasound signals into the pipe wall at at least one radiation angle which is inclined with respect to the normal to the pipe wall and the signals reflected at boundary regions of the pipe wall are received by same and/or other partial regions of the respective measuring sensors, wherein defects in the pipe wall are determined by evaluation of the acoustical signals reflected by different boundary regions.

18 Claims, 7 Drawing Sheets

METHOD AND DEVICE FOR INSPECTING PIPELINES

This application claims Paris Convention priority of DE 102 02 432.4 filed Jan. 22, 2002 the complete disclosure of which is hereby incorporated by reference.

BACKGROUND OF THE INVENTION

The invention concerns a method for inspecting pipelines, in particular for detecting material faults in pipelines using ultrasound, wherein measuring sensors transmit ultrasound signals during passage through a pipeline, and signals reflected on boundary regions, such as surfaces or defects of a pipe wall are measured and evaluated. The invention also concerns a device for inspecting pipelines, in particular as part of a device which is passed through a pipeline, with at least one sensor support having measuring sensors which are arranged substantially circularly around the sensor support.

Laid pipelines require regular automatized damage-free inspection for corrosion, pitting or the like. These defects can be determined by observation of associated pipe wall thickness variations and by their physical properties.

With appropriate radiation into the pipeline wall, the travel time differences between signals reflected on an inner wall and an outer wall as well as on defect locations in the pipeline are measured, the measurement results are tagged with a pipe section information, and are optionally intermediately stored for assessment after carrying out the test run and/or evaluated online. A device of this type is thereby usually connected to a component of the device for passing through the pipeline which has at least one pressure-tight housing for receiving means for processing and recording the measured value and for the supply of power.

EP 0 271 670 B2 discloses a method for detecting corrosion or the like on pipelines, wherein a device for inspecting the pipe walls is passed through a pipeline using a device for passing through a pipeline (pig) and transmits ultrasound signals whose travel time differences between reflection on the inner wall and outer wall of the pipeline is measured. The difference between these travel times determines the thickness of the pipe wall. Disadvantageously, small pittings are difficult to detect.

EP 0 255 619 B1 discloses a device to be moved through a pipeline for inspecting same which is provided with a circular support for ultrasound measuring heads transmitting ultrasound signals, which are disposed about the circumference of the support at regular intervals and having sensor surfaces which are always perpendicular to the normal to the pipe wall.

Disadvantageously, the above-described prior art method or device only detects corrosion and pitting, however not cracks. For detecting cracks extending up to the surface of a pipe, radiation must be applied at an angle and an additional run is required with a pig having sensors of different orientation. This only permits detection of cracks extending up to the surface of the pipe wall but not of cracks inside the wall.

It is therefore the underlying purpose of the present invention to produce a method and a device for inspecting pipelines, the device being of simple construction and reliably also detecting cracks in addition to surface corrosion and pitting, in particular cracks inside of the pipe wall and in a single measuring passage.

SUMMARY OF THE INVENTION

Throughout the description and claims of the instant invention, the term "virtual sensor" is defined as a group of sensor elements in a sensor arrangement of a plurality of sensor elements, the group of sensor elements occupying a partial region of that sensor arrangement.

This object is achieved in accordance with the invention in a method of the above-mentioned type in that partial regions of the measuring sensors (virtual sensors) formed by a plurality of adjacent sensor elements, radiate ultrasound signals into the pipe wall at a radiation angle inclined with respect to a normal to the pipe wall and the signals reflected by boundary regions of the pipeline are received by the same and/or other partial regions of the respective measuring sensors, with defects in the pipe wall being determined through evaluation of the acoustical signals reflected at different boundary regions. To achieve this object, a device of this type provides measuring sensors formed by sensor arrangements (virtual sensors) of a plurality of individual sensor elements, wherein each sensor element can be individually controlled.

The invention permits detection of corrosion and pitting as well as cracks and in particular cracks within the pipe wall using perpendicular and bi-directional inclined radiation. Detection of corrosion and pitting is effected through determination of travel time differences, since such changes in the pipe wall also produce a change in that travel time difference. The size of the (virtual) sensor can thereby be varied to also permit detection of (small) pittings. Cracks extending to the upper side of the wall are detected by the same detector combination due to their corner reflector response and using the pulse echo method. Detection of cracks inside of the wall is effected with the switch-through procedure using transducers which differ from the transmitting transducer combination. This also facilitates estimation of the depth.

The invention proposes the use of an ultrasound inspection method using so-called phased arrays for material testing in pipelines, wherein temporally variable individual control of single sensor elements permits comprehensive, high-resolution material testing. Moreover, the individual resilient sensor suspension preferably provided for each measuring sensor for cooperation with the inner wall of the pipeline can produce consistent quality of the signal radiated into the pipe wall and effect a defined position of the measuring sensors relative to the pipe wall. This is particularly important in pipelines, which usually have oval shapes, bulges or other non-circular shapes extending over long distances.

In a preferred embodiment, individual sensor elements of the measuring sensors, in particular individual sensor elements of a partial group of sensor elements of a measuring sensor forming a virtual sensor, are suitably controlled with temporal offset such that the propagation direction and/or focusing depth of the transmitted measuring pulse can be changed in the peripheral or radial direction. This permits, with each measuring sensor, radiation of a plurality of signals into the pipe wall at different radiation angles whose penetration behavior into the pipe wall can be largely adapted to the measuring requirements.

Signal irradiation and detection is preferably effected at a finite separation from the inner pipe wall to prevent damage to the measuring sensors by uneven pipe wall surfaces.

To obtain reliable and reproducible measurement results, the signal irradiation separation, i.e. the separation between a measuring sensor and the inner wall of the pipeline, is maintained substantially constant during the measurement.

Since cracks inside the pipe wall can only be reliably detected with signal radiation which is inclined relative to the normal to the pipe wall, a further embodiment of the invention provides that a signal irradiation direction, inclined relative to the normal to the pipe wall, is selected such that, after refraction at a boundary region between the pipe inner region and the pipe wall, the acoustical wave propagates at an angle of approximately 45° relative to the normal to the pipe wall. This path of the beam within the pipe wall ensures that reflection of the acoustical wave at the outer wall or inner wall of the pipe substantially produces total reflection of the acoustical wave, wherein the impinging and reflected beam assume an angle of 90° with respect to each other. Beam intensity is not externally refracted into the surroundings and a large part of the irradiated acoustical energy is radiated back towards the inner pipe region or inner pipe wall. This permits minimization of the acoustical energy required for carrying out the testing method.

Since cracks cannot always be reliably detected from one side (e.g. when the crack is in the vicinity of a pipe wall joint), irradiation must be effected from both sides. Towards this end, the signal is irradiated in accordance with the invention at a first and at a second angle, wherein the second angle results from mirroring the first angle about the normal to the pipe wall.

The individual sensor elements of a measuring sensor are preferably disposed in a linear array, with the array extending perpendicularly to the sensor surfaces, i.e. the signal irradiating or acoustically sensitive surfaces of the sensor elements. In a particularly preferred embodiment of the invention, the sensor arrays have a finite curvature in the direction of extension which is adjusted to the curvature of the pipe wall. In this fashion, each individual sensor element has a substantially same separation from the pipe inner wall.

To prevent collisions between neighboring measuring sensors due to the individually resilient coupling of the measuring sensors to the pipe wall, a preferred embodiment of the invention provides that a plurality of measuring sensors is disposed as a group at a common axial position with separations from each other in the peripheral direction. Preferably, the sensor elements of a group of measuring sensors are disposed on a circle which is concentric with the inner circumference of the pipe wall. To guarantee complete signal coverage of the pipe wall in the peripheral direction, a plurality of groups of measuring sensors can be provided which are mutually offset in the axial direction and which partially overlap in the peripheral direction. The degree of overlapping in the peripheral direction should be selected such that the signal coverage of the pipe wall in the peripheral direction is complete in conjunction with the above-described inclined signal irradiation.

To achieve complete signal coverage of the pipe wall during irradiation of the signals, different partial regions (virtual sensors) of the measuring sensors are controlled sequentially and repeatedly. Each partial region preferably has the same number of sensor elements such that an irradiating partial region of the measuring sensors is effectively temporally displaced along the measuring sensor until all sensor elements of each individual measuring sensor have been activated at least once. Such division of the measuring sensors into virtual subdivisions and the above-described virtual displacement of these units permits scanning of the pipe wall through a defined peripheral region.

The arrangement of the measuring sensors in the peripheral direction of the pipe wall advantageously ensures that signals reflected on the inner or outer pipe walls can be detected in a partial region of the transmitting measuring sensor, even when the signal is irradiated at an inclination, wherein the partial region generally differs from the partial region from which the signal was transmitted. In accordance with the invention, the above-described offset overlapping arrangement of a plurality of measuring sensors provides complete signal coverage of the pipe wall in the peripheral direction through the entire irradiation of all partial regions (virtual sensors) of all measuring sensors.

In view of the above, the pipe wall is completely scanned by signals due to a defined geometrical arrangement of the measuring sensors. In accordance with a further preferred embodiment of the invention, the measuring sensors can be rotated to provide complete signal coverage of the pipe wall in the peripheral direction of the pipeline. This inventive design comprises merely one group of measuring sensors disposed in a temporally varying axial position caused by movement of the device, which are separated from each other in the peripheral direction. The sensors rotate as a group about the pipe axis and are simultaneously moved in the axial direction due to the axial movement of the pig such that, at a suitable rotational speed, the pipe wall is completely scanned by the signals.

In a preferred embodiment of the invention, the sensor support has at least one central circular cylindrical central element which is disposed coaxially to the measuring sensors, for mounting the measuring sensors. To axially guide the device in the pipeline and to guarantee sufficient stability against tilting, the sensor support can have a guiding disc of circular cross-section which is disposed concentrically to the longitudinal axis and is flexible at least in its edge region and whose largest diameter corresponds to or slightly exceeds an inner diameter of the pipeline. A guiding disc of this design permanently abuts the inner wall of the pipeline during passage of the device and adjusts to the regular non-circular shapes of the pipeline due to its elastic edge region to guarantee safe guidance of the sensor arrangement. For sufficient wear resistance, the invention provides that the guiding disc be made from a suitable plastic material, in particular polyurethane.

In a preferred embodiment of the invention, the sensor suspension of the individual measuring sensors consists of at least two articulated arms which are joined to each other and whose free ends are each hinged to a mounting element of a sensor rocker receiving the measuring sensor or to the central element of the sensor support to guarantee flexible individual cooperation of the measuring sensors with the inner wall of the pipeline. The hinged connections may preferably be hinged joints. In this fashion, the individual measuring sensors can be displaced relative to the inner wall of the pipe in a radial and axial direction, whereas the position in the peripheral direction is more or less fixed.

To guarantee resilient coupling between the sensor arrays and the pipe wall while preventing bouncing of the articulated sensor suspension at non-circular shapes of the pipeline, e.g. at bulges as well as, in particular, radial oscillating motion of the sensor suspension, the invention furthermore provides that the articulated arm hinged to the central element is formed as telescopic spring element having additional damping properties. To improve the resilient and damping properties, a further telescopic spring element can be provided between the sensor rocker and elements of the sensor suspension.

The sensor rocker receives the array-shaped measuring sensors and is accordingly preferably formed such that a curvature of the surface facing the inner wall of the pipe of the sensor rockers in the peripheral direction corresponds substantially to the curvature of the sensor array. In a further embodiment of the invention, the sensor rockers have a surface groove extending in the peripheral direction into which the sensor arrays are fitted, wherein the depth of the groove corresponds substantially to a radial dimension of the sensor array. In accordance with a further preferred embodiment of the inventive device, the sensor rockers are oversized compared to an axial dimension of the sensor array. In a highly preferred embodiment, spacers are disposed in the oversized regions. This guarantees a fixed, final separation between the sensor arrays and the inner wall of the pipeline which improves the quality of the measuring results and also protects the measuring sensors, in particular from mechanical damage. In accordance with a further feature, the inventive device has a wear protection on the surface of the spacers facing the pipe wall to prolong the length of time during which the method and device in accordance with the invention can be used. The wear protection can consist e.g. of wear-resistant plastic material, e.g. polyurethane.

The material testing of pipelines in accordance with the invention is preferably effected using longitudinal ultrasound waves. In an extremely preferred embodiment of the invention, transverse waves can also be used for the material testing. This permits utilization of all possibilities of signal radiation and signal propagation in pipe walls for testing to reliably detect material defects which could otherwise have catastrophic consequences were they to remain undetected.

The invention is described below with reference to embodiments shown in the drawing.

DESCRIPTION OF THE PREFERRED EMBODIMENT

Figure 1:
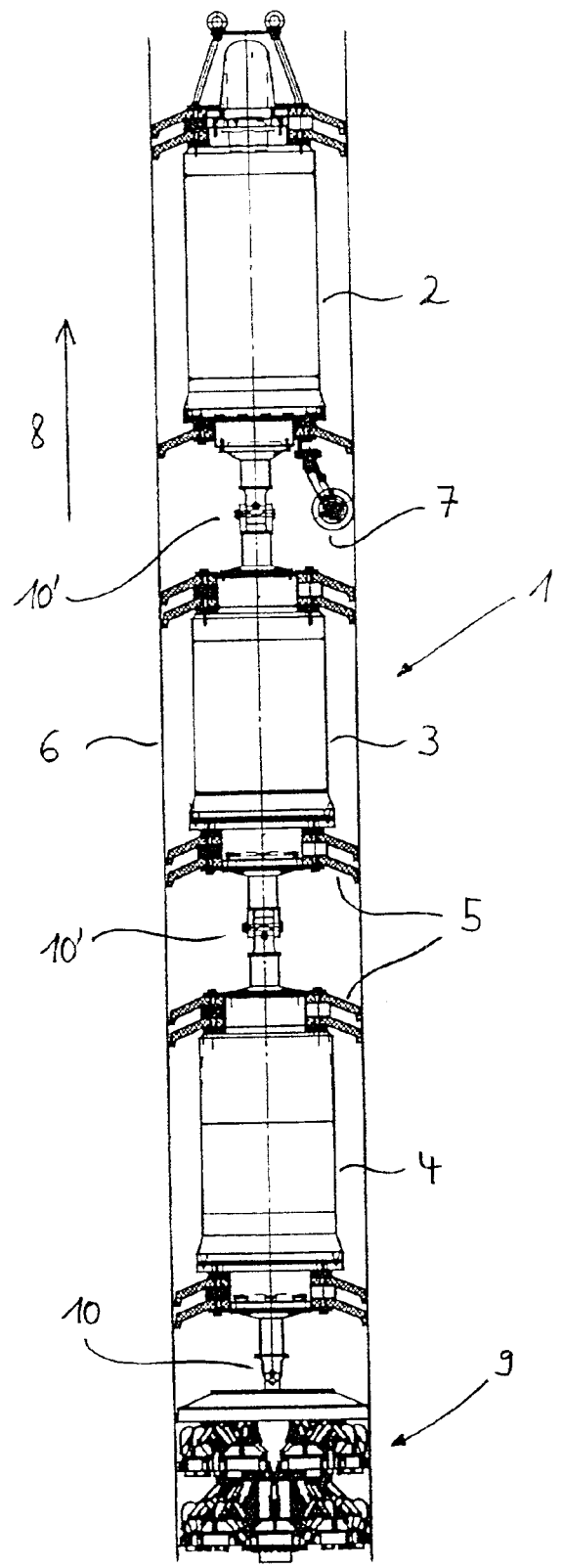
FIG. 1 shows a side view of a device for passage through a pipeline with an inventive device for inspection of same.

In the embodiment of FIG. 1, a device for passage through a pipeline, a so-called pig 1, comprises three sequential bodies 2, 3 and 4 each having one pressure-tight casing. The casings of the bodies 2, 3 and 4 have several collars 5 which abut the inside of the pipeline 6 to advance the pig 1 by means of the medium transported in the pipeline. Batteries are e.g. located in the casing of the body 2 for supplying the device with electricity. Moreover, the body 2 has at least one roller 7 constituting an odometer wheel for measurement of the path length. The casing of the second body 3 receives means for data processing and recording whereas the casing of the last downstream body 4 (direction of movement 8 of the device) comprises a measuring electronics for the sensor device described below.

The trailing end of the pig 1 of the embodiment shown in FIG. 1 comprises an inventive device 9 for inspecting pipelines with a sensor support and measuring sensors 16, 16' (FIG. 2) supported thereby. The individual bodies 2, 3 and 4 and the sensor support are interconnected via hinges 10, 10'.

Figure 2:
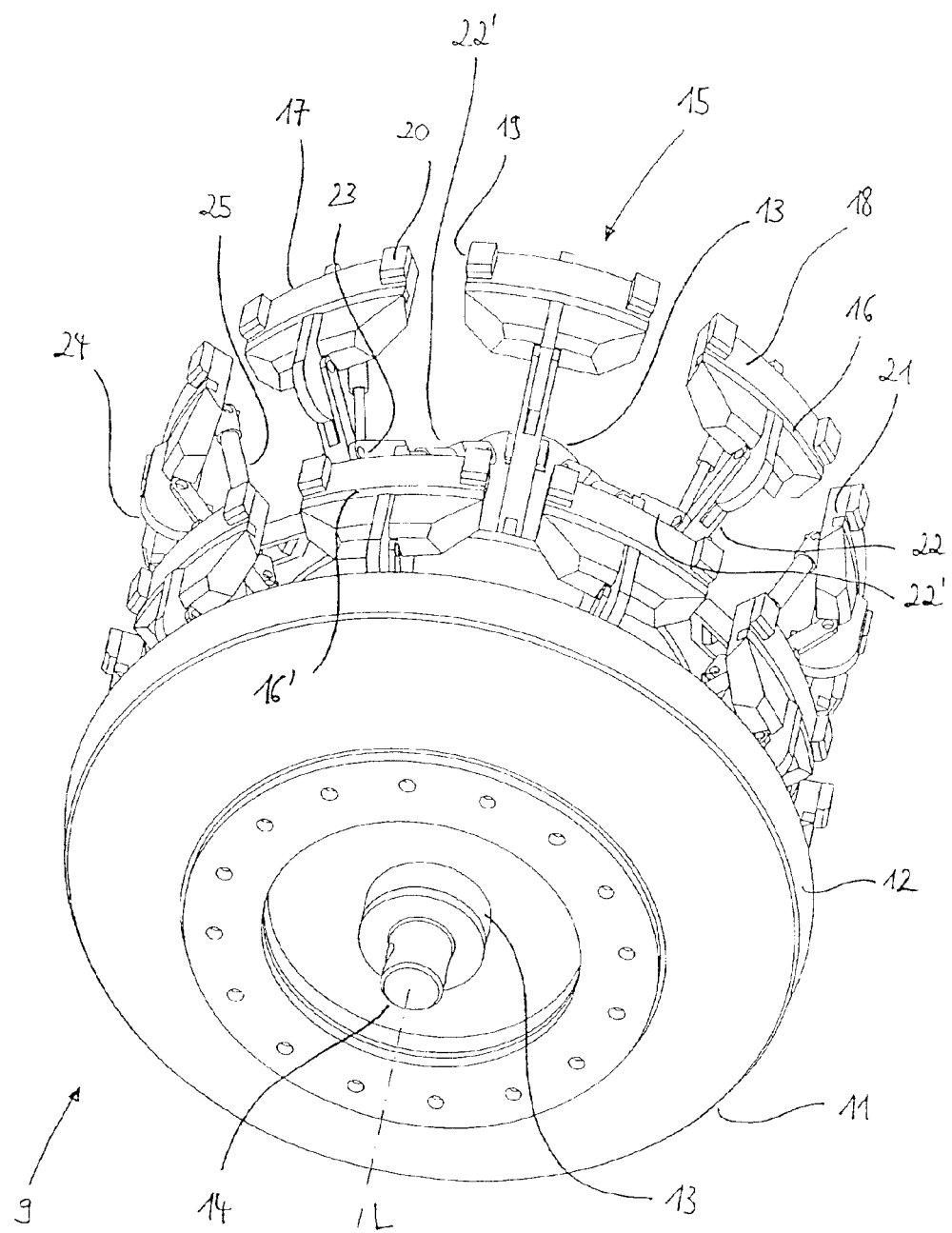
FIG. 2 shows a perspective view of an inventive device for inspecting pipelines.

FIG. 2 shows a perspective view of the inventive inspection device 9. Its front side comprises a guiding disc 11 which is elastic at least in its edge region 12 and preferably consists of polyurethane. The guiding disc 11 is disposed at one end of a cylindrically rod-shaped central element 13, the same end comprising an articulated element 14 which is designed to produce a hinged connection to an associated piece of the body 4.

A plurality of sensor suspensions 15 is disposed in two planes about the central element 13. Each of the sensor suspensions 15 comprises a sensor rocker 17 which receives the measuring sensors 16, 16'. The measuring sensors 16, 16' are disposed in two axially sequential groups which extend over the circumference wherein the sensors 16 of the one group partially overlap the sensors 16' of the other group in the peripheral direction to guarantee complete coverage of the entire circumference of the pipe wall by those sensors 16, 16', independent of a differing pipe diameters. The sensor rockers 17 have a surface 18 which is adjusted to the curvature of the pipe wall and which exceeds the corresponding extension of the measuring sensors 16, 16' in the axial direction, i.e. in the direction of the longitudinal axis L of the arrangement. The curved surface 18 of the sensor rockers 17 in the region of this oversize is provided with spacers 19 having wear protection on their upper sides 20. The measuring sensors 16, 16' are held in the sensor rockers 17 in a groove 21 fashioned in the upper side of the sensor rockers, wherein the measuring sensors 16, 16' and grooves 21 extend substantially in the peripheral direction.

The sensor suspensions 15 moreover comprise two articulated arms 22, 22' for producing a hinged mounting of the sensor rocker 17 to the central element 13. The articulated arms 22, 22' are interconnected by means of a hinge joint 23 and their respective free end is hinged to a mounting element 24 disposed on the sensor rocker 17 and on the central element 13 of the arrangement. A telescopic spring element 25 is provided between the lower side of the sensor rocker 17 and the lower articulated arm 22' of the sensor suspension 15 for producing an individually damped and resilient coupling of the sensor rocker 17 to the inner wall of the pipeline 6. In the embodiment shown, the lower articulated arm 22' is additionally formed as a telescopic spring element.

Due to their damping and resilient properties, the sensor suspensions 15 provide a defined separation between the measuring sensors 16, 16' and the inner wall of the pipeline 6 which is substantially constant during a measurement. The sensors 16, 16' do not thereby directly abut the inner wall of the pipeline 6 but are held by the spacers 19 at a certain finite separation. The sensors 16, 16' themselves and the sensor rockers 17 receiving them are formed such that they accommodate the curvature of the pipe wall.

FIG. 2 shows that the sensors 16, 16' are arranged in two groups each along a circle which is centrally disposed with respect to the axis L, wherein the sensors 16, 16' are spaced apart within a group in the peripheral direction to prevent collisions between sensors 16, 16' e.g. at cross-sectional narrowings. The sensors 16, 16' of different circular arrangements are thereby disposed relative to one another so as to "fill gaps" for achieving complete sensor coverage in the peripheral direction. The sensors transmit ultrasound via a radially directed narrow side and detect ultrasound signals scattered by the pipe wall.

Figure 3A:
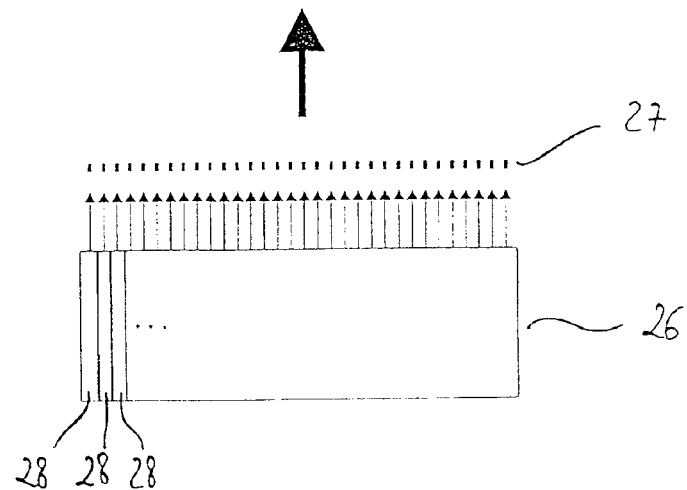
FIG. 3a shows a schematic view of the generation of an acoustical wave front propagating perpendicular to a sensor surface.

FIG. 3*a* shows a linear sensor arrangement 26 (sensor array) of individual sensor elements 28 of which only some are exemplarily shown.

Simultaneous triggering of all sensor elements 28 of such an array 26 produces a planar acoustical wave front 27 propagating perpendicular to the linear sensor arrangement 26 which, in the embodiment shown, is generated by the radiation of the individual sensor elements 28. If such an acoustical wave 27 is radiated along a normal N to the pipe wall 32 (see FIG. 7), the wave is reflected on the inner wall 33 of the pipeline 6 and also on the outer wall 34 of the pipeline 6 and can be detected by the substantially same transmitting sensor elements 28 (pulse echo method). A measured travel time difference between the two reflection signals determines the thickness of the pipe wall 32, wherein a wall thickness which is smaller than a desired value indicates corrosion damage.

Radial irradiation of ultrasound into the pipe wall is not suited for reliably detecting cracks with a generally radial extension component, rather irradiation should be effected at an angle.

Figure 3B:
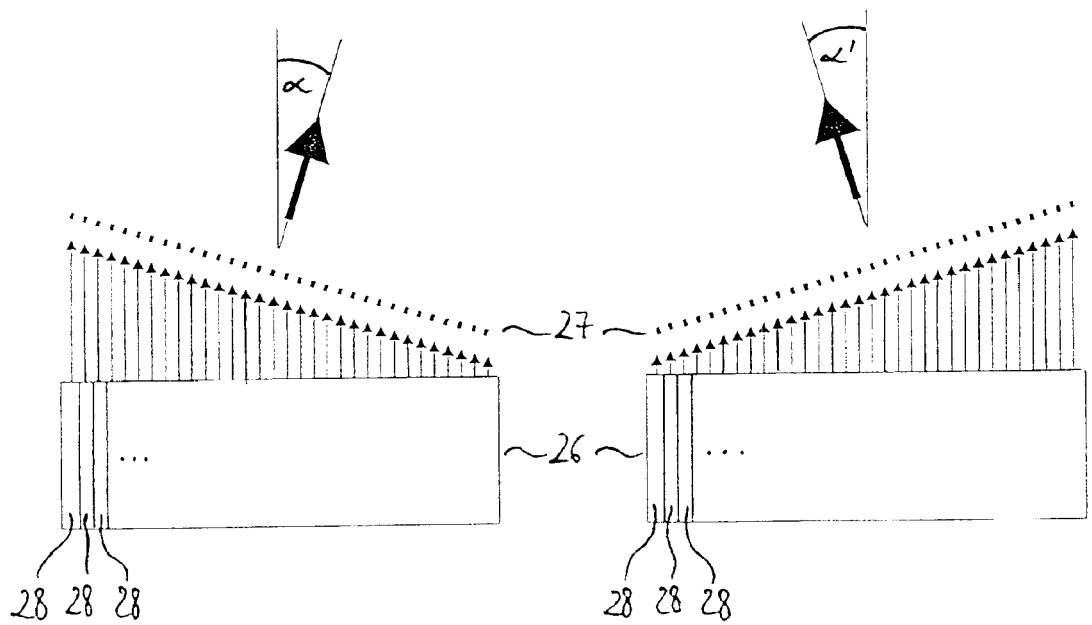
FIG. 3b shows a schematic view of the generation of an acoustical wave front propagating at an inclination with respect to a sensor surface.

FIG. 3*b* shows two examples of producing an inclined planar wave front 27 using a sensor arrangement 26 consisting of individual sensor elements 28. FIG. 3*b* shows that, when the individual sensor elements 28 are controlled with temporal delay, the sensor arrangements 26 emit a wave 27 which extends at a rightward angle α or a leftward angle α'. Temporally offset control of the sensor elements 28 is shown by arrows of different lengths above the individual sensor elements 28, wherein the length of the individual arrows illustrates the time elapsed since the triggering of the associated sensor element 28.

Numerous control variants of the sensor elements 28 are possible. By e.g. triggering sensor elements 28 from the edges of the sensor arrangement 26 towards a center thereof, a merging wave front 27 can be generated which i.e. focuses at a certain separation from the sensor arrangement 28.

Figure 4A:
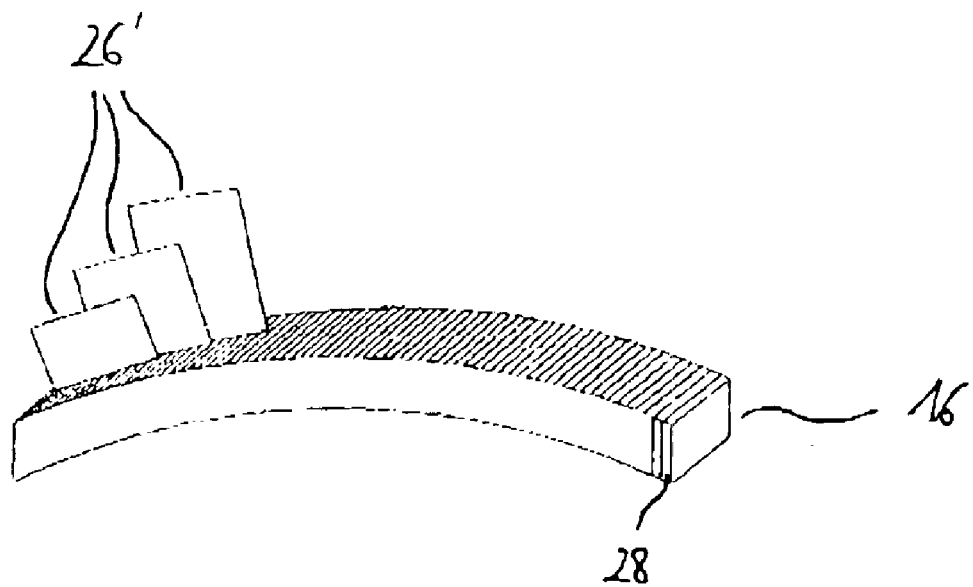
FIG. 4a shows a schematic representation of the subdivision of an inventive sensor into individual partial regions (virtual sensors)

FIG. 4*a* shows subdivision of an inventive measuring sensor 16, having a curvature adjusted to the pipe wall, into several partial regions 26', so-called virtual sensors, whose function corresponds to the sensor arrangements 26 discussed with reference to FIGS. 3*a* and 3*b*.

The inventive measuring sensors 16 can e.g. be formed of 256 individual sensor elements 28, 32 such sensor elements 28 can e.g. form one virtual sensor 26', wherein the virtual sensors 26' partially overlap to achieve sufficient resolution in the peripheral direction, i.e. each individual sensor element 28 can be associated with two virtual sensors.

Figure 4B:
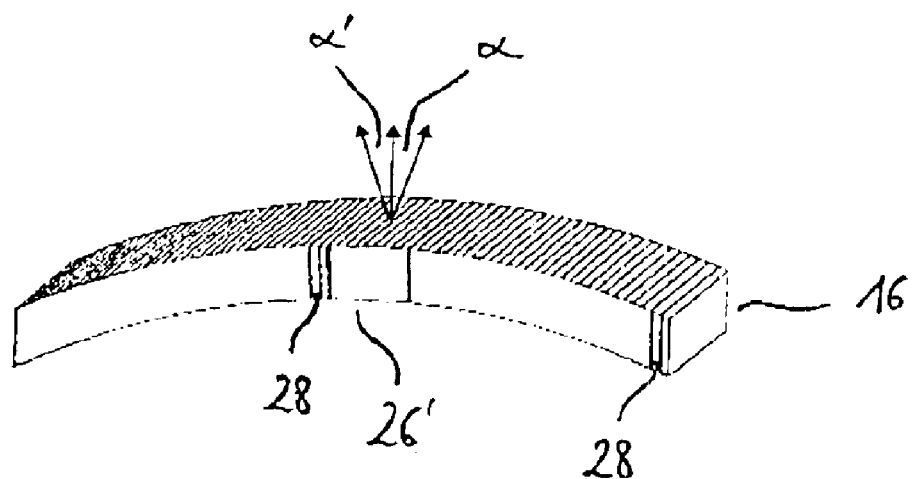
FIG. 4b shows a schematic representation of different possible acoustical radiation directions of a virtual sensor.

FIG. 4*b* illustrates the direction-selective radiation of a virtual sensor 26 formed from several sensor elements 28 of a sensor 16 as discussed with reference to FIGS. 3*a* and 3*b*. A virtual sensor 26' can be formed at each location of a measuring sensor 16 for irradiating ultrasound waves at any desired angle relative to a normal N to the pipe wall. In the embodiment shown, irradiation is effected at an angle of 0° and at two angles α, α' different from 0. In this fashion, the inventive measuring sensors 16 can be used for determining the wall thickness using the pulse echo method and also for detecting cracks, such as those of FIG. 7 (transmission technique).

Figure 5:
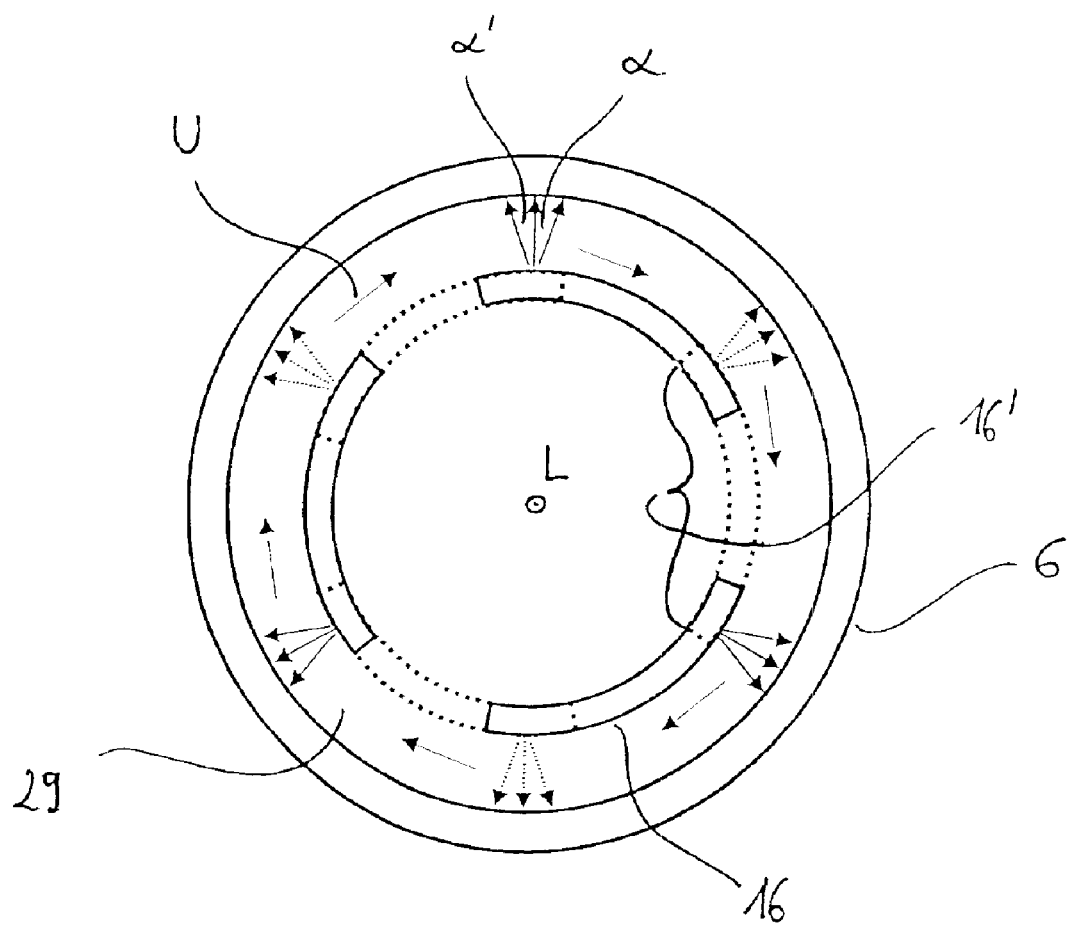
FIG. 5 shows a schematic sectional view of the arrangement of the inventive measuring sensors within a pipeline.

FIG. 5 shows how complete signal coverage of the pipeline 6 can be achieved by means of the arrangement of measuring sensors 16, 16' described in FIG. 2. FIG. 5 shows overlapping of the measuring sensors 16 of the first circular arrangement with the measuring sensors 16' of the second circular arrangement in the peripheral direction U. Each of the measuring sensors 16, 16' transmits, via a partial region (i.e. a virtual sensor) three rapidly sequential ultrasound signals at the three radiation angles 0°, α, α', usually such that the propagation of the wave front in the pipeline is effected at an angle of 45°, wherein α'=-α. Radiation is thereby effected at positive and negative angles with respect to the normal, since a crack located directly behind a pipe welding joint which is not detected in a first (positive) direction of radiation, can be reliably detected by the other (negative) inclined irradiation direction since it is thereby located in front of the pipe welding joint. The virtual sensors are then displaced in the peripheral direction (in the direction of the arrow U) by at least one sensor element 28, whereupon three ultrasound signals are again transmitted, respectively. In this fashion, the pipeline 6 is scanned in the peripheral direction U In the region of the sensors 16, 16' thereby producing, together with the mentioned sensor overlapping, complete signal coverage in the peripheral direction U. As shown in FIG. 5, the measuring sensors 16, 16' are disposed at a separation from the pipe wail, wherein the free space 29 remaining between the measuring sensors 16, 16' and the inner wall of the pipeline 6 is filled with the medium transported in the pipeline 6.

Figure 6A:
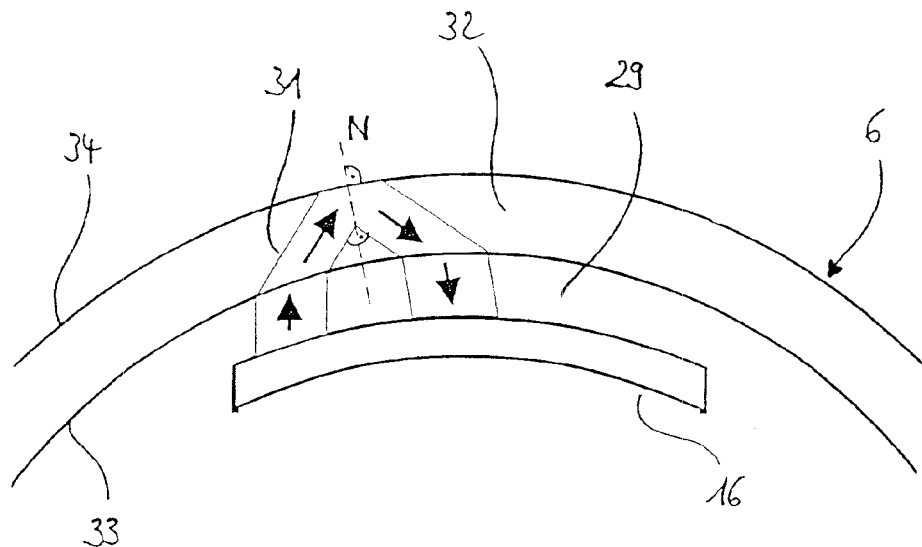
FIG. 6a shows a schematic representation of the acoustical path in a pipe wall without a crack.
Figure 6B:
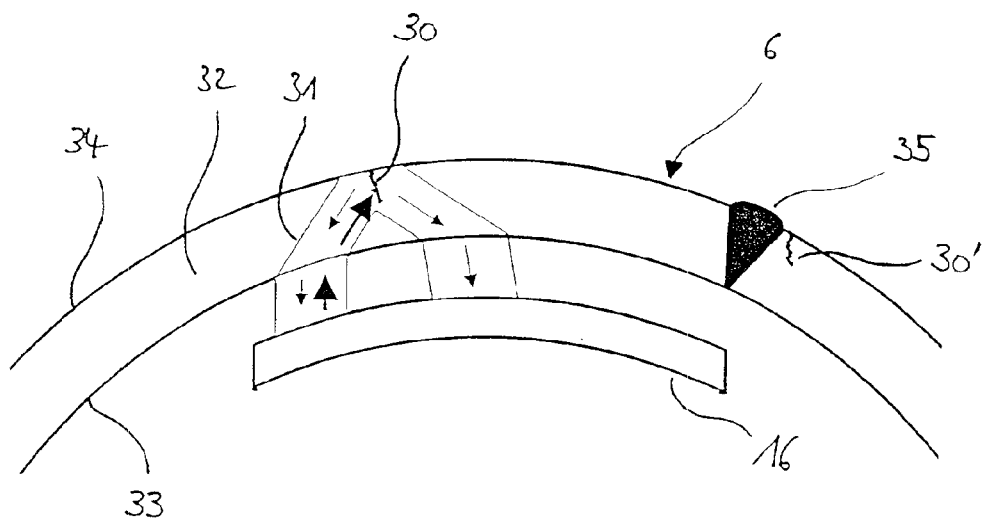
FIG. 6b shows a schematic view of the acoustical paths in a pipe wall with a crack.

FIGS. 6*a* and 6*b* show the inventive method for detecting cracks 30 inside the pipe wall 6.

FIG. 6*a* schematically shows the acoustical path 31 in the wall 32 of a pipeline 6. A partial region (virtual sensor) of a measuring sensor 16 disposed within the pipeline 6 irradiates an ultrasound wave which is inclined at a finite angle relative to a normal N to the pipe wall 32 and which passes into the pipe wall such that the wave front propagates at an angle of approximately 45° to the normal N to the pipe wall 32 following initial refraction on the inner wall 33 of the pipeline 6. This substantially guarantees total reflection of the radiated acoustical wave on the outer wall 34 of the pipeline 6 such that the entire irradiated energy is reflected back in the direction of the inner wall 33 of the pipeline 6. The acoustical wave then refracts on the inner wall 33 and, after passing the free space 29, impinges on the measuring sensor 16 at another partial region where it can be detected with an intensity which corresponds substantially to the irradiated intensity.

FIG. 6*b* shows a situation similar to that of FIG. 6*a*. In this embodiment, the crack 30 is in the vicinity of the outer wail 34 of the pipeline 6. In this case, part of the acoustical energy radiated analogously to FIG. 6*a* is reflected or refracted at the crack 30 and is detected in the region of the emitting virtual sensor of the measuring sensor 16. To be able to detect cracks 30' in regions which are difficult to access using ultrasound waves, e.g. in the vicinity of a pipe wall joint 35, radiation from both sides of each location of the pipe wall 32 is required. This is ensured by the inventive geometry of irradiation and the overlapping arrangement of the measuring sensors.

Figure 7:
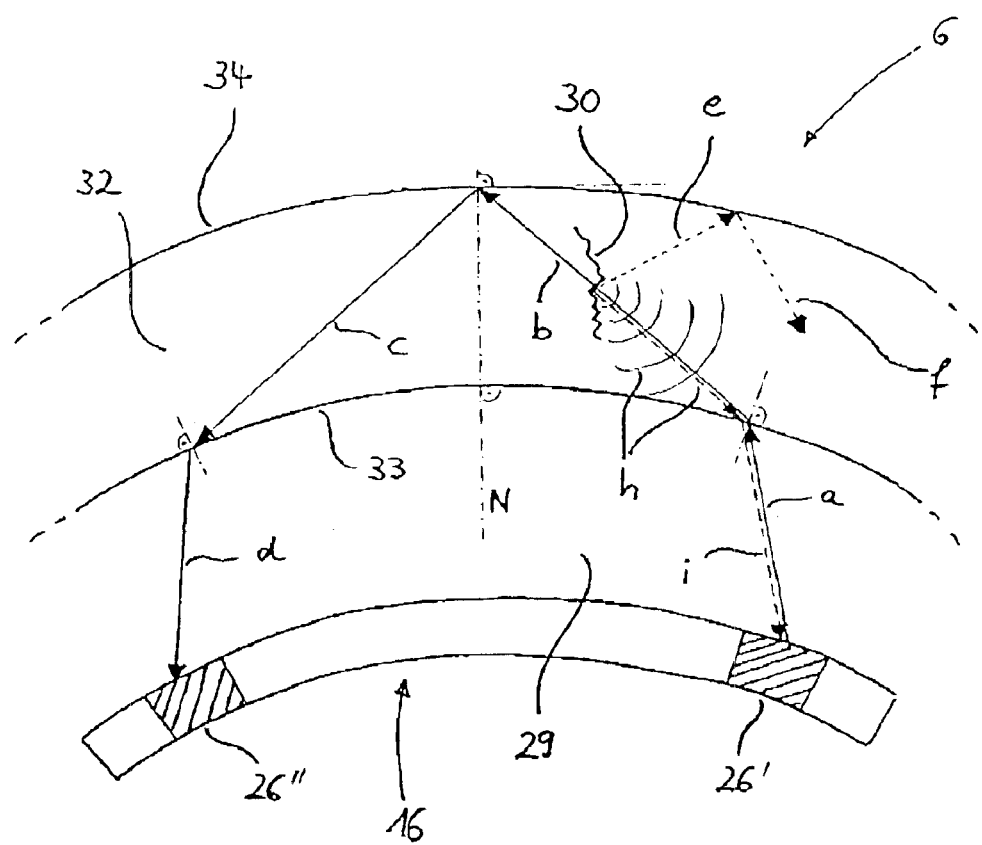
FIG. 7 shows a schematic representation of the paths of the acoustical signals which can be utilized for detecting a crack, in particular for estimating the crack depth.

FIG. 7 shows the interaction of an acoustical wave a radiated into the pipe wall 32 having a crack 30. The path of radiation a-b-c-d from an emitting virtual sensor 26' of the measuring sensor 16 to a virtual sensor 26' corresponds substantially to the acoustical path 31 shown in FIG. 6*a* (wherein in contrast to FIG. 6, FIG. 7 shows signal radiation from the right-hand side). Should the pipeline 6 have a crack 30, only part of the irradiated acoustical wave travels along the path a-b-c-d to the virtual sensor 26" and a portion of the wave energy (e,f) is refracted or reflected at the defective location 30. In the embodiment shown, this portion remains undetected. The portion h of the irradiated acoustical wave refracted at the crack 30 reaches the partial region 26 (virtual sensor) of the measuring sensor 16 along the path h-i (see FIG. 7).

List of Reference Numerals
1 pig
2,3,4 (pig) body
5 collar
6 pipeline
7 roller
8 direction of movement of the pig (1)
9 testing device
10,10' hinge
11 guiding disc
12 edge region
13 central element
14 hinged element
15 sensor suspension
16,16' measuring sensor
17 sensor rocker
18 surface of the sensor rocker (17)
19 spacer
20 upper side of the spacer (19)
21 groove
22,22' articulated arms
23 hinge joint
24 mounting element
25 telescopic spring element
26 sensor arrangement
26',26" virtual sensor
27 acoustical wave front
28 sensor element
29 free space
30,30' crack
31 acoustical travel path
32 pipe wall
33 inner wall
34 outer wall
35 pipe wall joint
L (longitudinal) axis
N normal to pipe wall
U peripheral direction
α,α' radiation angle

We claim:

1. A device for inspecting the pipe wall of a pipeline for defects, the device comprising:
means for introducing a plurality of measuring sensors into the pipeline, each measuring sensor comprising at least one linear array of individually controllable sensor elements;
means for defining a plurality of virtual sensors, each virtual sensor comprising a group of neighboring sensor elements;
means for individually controlling said sensor elements of at least a portion of said virtual sensors to generate an ultrasound wave travelling towards and into said pipe wall at an irradiation angle which is inclined relative to a normal to the pipe wall;
means for receiving ultrasound signals reflected by bordering surfaces of the pipe wall in at least a portion of said virtual sensors; and
means for evaluating said received signals from differing bordering surfaces to determine pipe wall defects and further comprising at least one sensor support having said measuring sensors disposed substantially circularly around said sensor support, wherein said sensor support comprises, for each measuring sensor, at least two articulated arms which are hinge connected to each other and whose free end is hinge connected to one of a mounting element of a sensor rocker receiving said measuring sensor and to a central element of said sensor support, wherein said measuring sensors are fitted into a groove in an upper surface of said sensor rockers extending in a peripheral direction, wherein a depth of said groove corresponds substantially to a radial dimension of said measuring sensors.

2. The device of claim 1, further comprising at least one resilient sensor suspension for each measuring sensor to urge said measuring sensors towards an inner wall of the pipeline.

3. The device of claim 1, wherein said measuring sensors have a curvature along an extension in a peripheral direction which is adapted to a curvature of the pipe wall.

4. The device of claim 1, wherein a plurality of measuring sensors is disposed as a group at a common axial position, wherein said plurality of measuring sensors have mutual separations in a peripheral direction.

5. The device of claim 4, wherein sensor elements of one group of measuring sensors are disposed on a circle which is concentric to an inner periphery of the pipe wall.

6. The device of claim 5, wherein said measuring sensors can be rotated in said peripheral direction along a circle which is concentric to an inner periphery of the pipe wail.

7. The device of claim 4, wherein a plurality of groups of measuring sensors are offset with respect to each other in an axial direction and in said peripheral direction, wherein said measuring sensors partially overlap in said peripheral direction.

8. The device of claim 1, wherein said controlling means trigger temporally offset control of individual sensor elements of said measuring sensors to change at least one of a direction of propagation and a focusing depth of a measurement pulse in at least one of said peripheral direction and a radial direction.

9. The device of claim 1, wherein said sensor support has at least one central circular cylindrical element disposed coaxially to said measuring sensors for mounting thereof.

10. The device of claim 1, further comprising a guiding disc disposed concentrically with respect to a longitudinal axis, said guiding disc being flexible at least in an edge region thereof and having a circular cross-section whose largest diameter is at least as large as an inner diameter of the pipeline.

11. The device of claim 10, wherein said guiding disc comprises one of a plastic material and polyurethane.

12. The device of claim 1, wherein said hinge connections are hinge joints.

13. The device of claim 1, wherein one of said at least two articulated arms is hinged to said central element to form a first telescopic spring element.

14. The device of claim 13, further comprising a second telescopic spring element disposed between said sensor rocker and elements of a sensor suspension.

15. The device of claim 1, wherein said sensor rockers are formed such that a curvature in a peripheral direction of surfaces thereof facing the pipe wall substantially corresponds to a curvature of said measuring sensors.

16. The device of claim 1, wherein said sensor rockers have an axial length which exceeds that of said measuring sensors.

17. The device of claim 16, further comprising spacers disposed on said sensor rockers at a region of said excess axial length.

18. The device of claim 17, wherein said spacers have a wear protection at upper sides thereof facing the pipe wall.

* * * * *